US008637644B2

(12) United States Patent
Ho et al.

(10) Patent No.: US 8,637,644 B2
(45) Date of Patent: Jan. 28, 2014

(54) H5 SUBTYPE-SPECIFIC BINDING PROTEINS USEFUL FOR H5 AVIAN INFLUENZA DIAGNOSIS AND SURVEILLANCE

(75) Inventors: Yuen Fern Ho, Singapore (SG); Qing Yun Du, Singapore (SG); Fang He, Shanghai (CN); Jimmy Hwei-Sing Kwang, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 0 days.

(21) Appl. No.: 13/613,767

(22) Filed: Sep. 13, 2012

(65) Prior Publication Data

US 2013/0004943 A1 Jan. 3, 2013

Related U.S. Application Data

(63) Continuation of application No. 12/599,616, filed as application No. PCT/SG2007/000134 on May 11, 2007, now Pat. No. 8,540,994.

(51) Int. Cl.
*A61K 39/395* (2006.01)
*C12Q 1/70* (2006.01)
*C07K 16/10* (2006.01)
*C12N 7/00* (2006.01)
*G01N 33/569* (2006.01)
*G01N 33/577* (2006.01)
*A61K 39/145* (2006.01)

(52) U.S. Cl.
USPC .................. 530/388.3; 424/130.1; 424/184.1; 424/209.1; 435/5; 435/235.1; 530/387.1; 530/388.2; 530/389.4

(58) Field of Classification Search
USPC ...................... 424/130.1, 184.1; 435/5, 235.1; 530/387.1, 388.2, 388.3, 389.4
See application file for complete search history.

(56) References Cited

U.S. PATENT DOCUMENTS

| 8,383,121 | B2 * | 2/2013 | Qian et al. | 424/147.1 |
|---|---|---|---|---|
| 2007/0003576 | A1 * | 1/2007 | Gambotto et al. | 424/209.1 |
| 2007/0031453 | A1 * | 2/2007 | Hoffmann et al. | 424/209.1 |
| 2007/0065452 | A1 * | 3/2007 | Schiltz et al. | 424/159.1 |
| 2007/0087339 | A1 * | 4/2007 | Sampath et al. | 435/5 |
| 2007/0087340 | A1 * | 4/2007 | Sampath et al. | 435/5 |
| 2007/0087341 | A1 * | 4/2007 | Sampath et al. | 435/5 |
| 2007/0092524 | A1 * | 4/2007 | Nusbacher et al. | 424/159.1 |
| 2009/0068637 | A1 * | 3/2009 | Xia et al. | 435/5 |
| 2010/0266585 | A1 * | 10/2010 | Qian et al. | 424/133.1 |
| 2010/0297126 | A1 * | 11/2010 | Qian et al. | 424/135.1 |
| 2011/0003278 | A1 * | 1/2011 | Ho et al. | 435/5 |
| 2011/0053142 | A1 * | 3/2011 | Mookkan et al. | 435/5 |
| 2011/0256141 | A1 * | 10/2011 | Mookkan et al. | 424/135.1 |
| 2012/0045473 | A1 * | 2/2012 | Kwang | 424/210.1 |
| 2013/0004496 | A1 * | 1/2013 | Qian et al. | 424/135.1 |
| 2013/0004497 | A1 * | 1/2013 | Qian et al. | 424/135.1 |

FOREIGN PATENT DOCUMENTS

WO 2008060331 A2 5/2008

OTHER PUBLICATIONS

Yoshida R, Igarashi M, Ozaki H, Kishida N, Tomabechi D, Kida H, Ito K, Takada A. Cross-protective potential of a novel monoclonal antibody directed against antigenic site B of the hemagglutinin of influenza A viruses. PLoS Pathog. Mar. 2009;5(3):e1000350. Epub Mar. 20, 2009.*
Daniels PS, Jeffries S, Yates P, Schild GC, Rogers GN, Paulson JC, Wharton SA, Douglas AR, Skehel JJ, Wiley DC. The receptor-binding and membrane-fusion properties of influenza virus variants selected using anti-haemagglutinin monoclonal antibodies. EMBO J. May 1987;6(5):1459-65.*
Khurana S, Suguitan AL Jr, Rivera Y, Simmons CP, Lanzavecchia A, Sallusto F, Manischewitz J, King LR, Subbarao K, Golding H. Antigenic fingerprinting of H5N1 avian influenza using convalescent sera and monoclonal antibodies reveals potential vaccine and diagnostic targets. PLoS Med. Apr. 21, 2009;6(4):e1000049. Epub Apr. 21, 2009.*
Toebes M, Coccoris M, Bins A, Rodenko B, Gomez R, Nieuwkoop NJ, van de Kasteele W, Rimmelzwaan GF, Haanen JB, Ovaa H, Schumacher TN. Design and use of conditional MHC class I ligands. Nat Med. Feb. 2006;12(2):246-51. Epub Feb. 5, 2006.*
Hanson BJ, Boon AC, Lim AP, Webb A, Ooi EE, Webby RJ. Passive immunoprophylaxis and therapy with humanized monoclonal antibody specific for influenza A H5 hemagglutinin in mice. Respir Res. Oct. 14, 2006;7:126.*
He F, Du Q, Ho Y, Kwang J. Immunohistochemical detection of Influenza virus infection in formalin-fixed tissues with anti-H5 monoclonal antibody recognizing FFWTILKP. J Virol Methods. Jan. 2009;155(1):25-33. doi: 10.1016/j.jviromet.2008.09.016. Epub Nov. 7, 2008.*
He Q, Velumani S, Du Q, Lim CW, Ng FK, Donis R, Kwang J. Detection of H5 avian influenza viruses by antigen-capture enzyme-linked immunosorbent assay using H5-specific monoclonal antibody. Clin Vaccine Immunol. May 2007;14(5):617-23. Epub Mar. 7, 2007.*
Velumani S, Du Q, Fenner BJ, Prabakaran M, Wee LC, Nuo LY, Kwang J. Development of an antigen-capture ELISA for detection of H7 subtype avian influenza from experimentally infected chickens. J Virol Methods. Feb. 2008;147(2):219-25. Epub Oct. 24, 2007.*
Philpott M, Hioe C, Sheerar M, Hinshaw VS. Hemagglutinin mutations related to attenuation and altered cell tropism of a virulent avian influenza A virus. J Virol. Jun. 1990;64(6):2941-7.*

(Continued)

*Primary Examiner* — Benjamin P Blumel
*Assistant Examiner* — Rachel Gill
(74) *Attorney, Agent, or Firm* — Rothwell, Figg, Ernst & Manbeck P.C.

(57) ABSTRACT

The invention provides monoclonal antibodies and related binding proteins that bind specifically to the envelope glycoprotein of H5 subtypes of avian influenza virus ("AIV"). The monoclonal antibodies and related binding proteins are useful for the detection of H5 subtypes of AIV, including the pathogenic H5N1 subtypes. Virus may be detected in formalin preserved, paraffin embedded specimens as well as frozen specimens and biological fluids. Accordingly, the invention provides for the diagnosis and surveillance of dangerous viral infections.

11 Claims, 6 Drawing Sheets

(56) References Cited

OTHER PUBLICATIONS

Philpott M, Easterday BC, Hinshaw VS. Neutralizing epitopes of the H5 hemagglutinin from a virulent avian influenza virus and their relationship to pathogenicity. J Virol. Aug. 1989;63(8):3453-8.*

Smirnov, Y.A., et al., "Prevention and treatment of bronchopneumonia in mice caused by mouse-adapted variant of avian H5N2 influenza A virus using monoclonal antibody against conserved epitope in the HA stem region," Archives of Virology, 145: 1733-1741 (2000).

Smirnov, Y.A., et al., "An Epitope Shared by the Hemagglutinins of H1, H2, H5 and H6 Subtypes of Influenza A Virus," Acta Virologics, 43: 237-244 (1999).

He, Yuxan, et al., "Receptor-Binding Domain of Severe Acute Respiratory Syndrome Coronavirus Spike Protein Contains Multiple Conformation-Dependent Epitopes that Induce Highly Potent Neutralizing Antibodies," The Journal of Immunology, 174(8): 4908-4915 (2005).

Tarnovitski, Natalia, et al., "Mapping a Neutralizing Epitope on the SARS Coronavirus Spike Protein: Computational Prediction Based on Affinity-selected Peptides," Journal Molecular Biology, 359: 190-201 (2006).

European Patent Office, Partial Search Report dated Jul. 22, 2011 for EP Appln 11152706.5.

Lyon, Jeffrey A., et al., Monoclonal Antibody Characterization of the 195-Kilodalton Major Surface Glycoprotein of Plasmodium falciparum Malaria Schizonts and Merozoites: Identification of Additional Processed Products and a Serotype-Restricted Repetitive Epitope; The Journal of Immunology, 138(30): 895-901 (Feb. 1, 1987).

Breschkin, A.M., et al., "Antigenic Determinants of Influenza Virus Hemagglutinin," Virology, 113(1): 130-140 (Aug. 1, 1981).

Chen, Jianfeng, et al,. A latex agglutination test for the rapid detection of avian influenza virus subtype H5N1 and its clinical application, J. Vet. Diagn. Invest., 19(2): 155-160 (Mar. 1, 2007).

Kaverin, Nikolai, V., et al., "Structure of antigenic sites on the haemagglutinin molecule of H5 avian influenza virus and phenotypic variation of escape mutants," Journal of General Virology, 83(10): 2497-2505 (Oct. 2002).

European Patent Office, Supplementary European Search Report dated May 18, 2010 for EP 07748679.3.

Huang, Hongliang, et al., "Different neutralization efficiency of neutralizing monoclonal antibodies against avian influenza H5N1 virus to virus strains from different hosts," Molecular Immunology, 44: 1052-1055 (2007)

Il'Yushina, N.A., et al., "Antigenic Structure of Influenza A Virus Subtype H5 Hemagglutinin: Mechanism of the Acquisition of Resistance to Monoclonal Antibodies in Escape Mutants," Molecular Genetics, Microbiology and Virology, 2:21-27 (2003).

English translation of Japanese Office Action (drafting date Aug. 1, 2012), JP Application No. 2010-508341, 6 pages.

* cited by examiner

| Clone No. | mAb isotype | H5 subtype AIV | | | Non-H5 subtype | | | | |
|---|---|---|---|---|---|---|---|---|---|
| | | H5N1 | H5N2 | H5N3 | H3N2 | H4N1 | H7N1 | H9N2 | H10N5 |
| 6B8 | IgM | | | | | | | | |
| 7H10 | IgM | | | | | | | | |
| 2D10 | IgM | | | | | | | | |
| 8F10 | IgM | | | | | | | | |
| 2E6 | IgG1 | | | | | | | | |
| 2G8 | IgG1 | | | | | | | | |

Figure 3

2D10  6B8  8F10  7H10 Control

← HA1 protein (36 kDa)

HA1 (A/goose/Guangdong/97 H5N1)

| Segment | Range | Western Blot |
|---|---|---|
| HA1 | 1–338 | + |
| A | 1–133 | — |
| B | 67–266 | + |
| C | 201–338 | + |
| D | 67–248 | — |
| E | 67–253 | + |
| F | 67–240 | — |
| G | 67–244 | — |
| H | 67–252 | + |
| I | 67–249 | — |
| J | 67–251 | + |
| K | 67–250 | — |

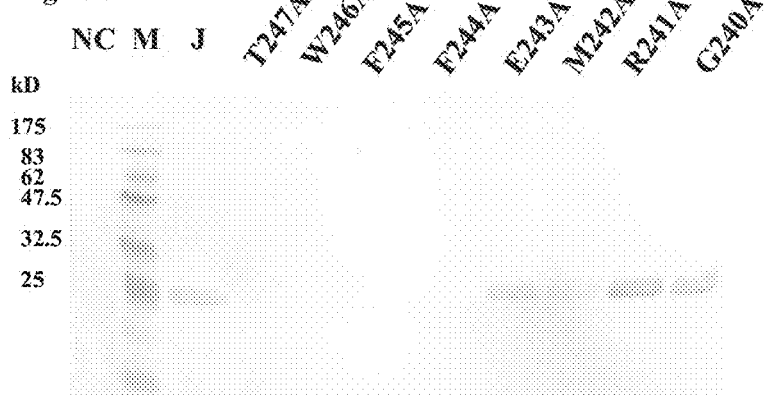

```
SEQUENCE LISTING

<160> NUMBER OF SEQ ID NOS: 9

<210> SEQ ID NO 1
<211> LENGTH: 12
<212> TYPE: PRT
<213> ORGANISM: Avian influenza virus

<400> SEQUENCE: 1

Gly Arg Met Glu Phe Phe Trp Thr Ile Leu Lys Pro
1               5                   10

<210> SEQ ID NO 2
<211> LENGTH: 12
<212> TYPE: PRT
<213> ORGANISM: Avian influenza virus

<400> SEQUENCE: 2

Gly Arg Met Glu Phe Phe Trp Ala Ile Leu Lys Pro
1               5                   10

<210> SEQ ID NO 3
<211> LENGTH: 12
<212> TYPE: PRT
<213> ORGANISM: Avian influenza virus

<400> SEQUENCE: 3

Gly Arg Met Glu Phe Phe Ala Thr Ile Leu Lys Pro
1               5                   10

<210> SEQ ID NO 4
<211> LENGTH: 12
<212> TYPE: PRT
<213> ORGANISM: Avian influenza virus

<400> SEQUENCE: 4

Gly Arg Met Glu Phe Ala Trp Thr Ile Leu Lys Pro
1               5                   10

<210> SEQ ID NO 5
<211> LENGTH: 12
<212> TYPE: PRT
<213> ORGANISM: Avian influenza virus

<400> SEQUENCE: 5

Gly Arg Met Glu Ala Phe Trp Thr Ile Leu Lys Pro
1               5                   10
```

```
<210> SEQ ID NO 6
<211> LENGTH: 12
<212> TYPE: PRT
<213> ORGANISM: Avian influenza virus

<400> SEQUENCE: 6

Gly Arg Met Ala Phe Phe Trp Thr Ile Leu Lys Pro
1               5                   10

<210> SEQ ID NO 7
<211> LENGTH: 12
<212> TYPE: PRT
<213> ORGANISM: Avian influenza virus

<400> SEQUENCE: 7

Gly Arg Ala Glu Phe Phe Trp Thr Ile Leu Lys Pro
1               5                   10

<210> SEQ ID NO 8
<211> LENGTH: 12
<212> TYPE: PRT
<213> ORGANISM: Avian influenza virus

<400> SEQUENCE: 8

Gly Ala Met Glu Phe Phe Trp Thr Ile Leu Lys Pro
1               5                   10

<210> SEQ ID NO 9
<211> LENGTH: 12
<212> TYPE: PRT
<213> ORGANISM: Avian influenza virus

<400> SEQUENCE: 9

Ala Arg Met Glu Phe Phe Trp Thr Ile Leu Lys Pro
1               5                   10
```

H5 SUBTYPE-SPECIFIC BINDING PROTEINS USEFUL FOR H5 AVIAN INFLUENZA DIAGNOSIS AND SURVEILLANCE

CROSS-REFERENCE TO RELATED APPLICATIONS

The present application is a continuation of U.S. patent application Ser. No. 12/599,616 filed 22 Sep. 2010, which in turn is a filing under 35 USC 371 of PCT/SG2007/000134, filed 11 May 2007. Each application is incorporated herein in its entirety.

SEQUENCE SUBMISSION

The present application contains a Sequence Listing in electronic format. The Sequence Listing is entitled 2577221 SequenceListing.txt, created on 7 Sep. 2012 and is 3 kb in size and filed on 9 Oct. 2012. The information in the electronic format of the Sequence Listing is incorporated herein by reference in its entirety.

FIELD OF THE INVENTION

This invention relates to antibodies and related binding proteins for the detection of avian influenza virus ("AIV"). More particularly, the invention relates to monoclonal antibodies and related binding proteins useful for the detection of the highly pathogenic H5 subtypes of AIV and to methods and products for the diagnosis and surveillance of such AIV infections in animals and humans.

BACKGROUND OF THE INVENTION

Avian influenza is a common disease in birds. Subtype H5N1 AIV has caused an outbreak of avian influenza that is spreading incessantly to many regions of the world (14). The affected areas include Europe, the Middle East and particularly Asia. According to the World Health Organization ("WHO"), as of April 2006, about one hundred human deaths had occurred as a result of H5N1 avian influenza, and the situation seems to be deteriorating. See WHO website (11). While AIV infection in humans is rare, there have been times in the past in which the occurrence of new AIV subtypes that are able to cross species barriers have caused deadly influenza pandemics (2, 8, 10).

Influenza viruses are classified according to their nucleoprotein and matrix protein antigenic specificity. These viruses are categorized mainly into A, B and C serotypes, with type A having eight RNA segments that encode ten viral proteins. All known type A influenza viruses originated in birds. This category of virus can infect other species, such as horses, pigs, owls and seals, and poses a threat to humans as well (22). Influenza A virus is further divided into subtypes according to the antigenic nature of the envelope glycoproteins, hemagglutinins ("HAs"), H1 through H16, and neuraminidases ("NAs"), N1 through N9 (10, 12, 19). It is believed that proteolytic cleavage of HA protein at the HA1-HA2 junction is related to the pathogenicity in avian strain and that the presence of hydrophobic amino acids around this cleavage site are characteristic of the H5 subtype. In addition, the HA protein is believed to mediate attachment to host cell sialoside receptors and subsequent entry by membrane fusion (17), and HA protein is thought to serve as a primary target for neutralizing antibodies (19).

This invention relates to monoclonal antibodies and related binding proteins that bind specifically to AIV. Monoclonal antibodies ("mAbs") are a substantially homogeneous population of antibodies derived from a single antibody-producing cell. Thus all antibodies in the population are identical and of the same specificity for a given epitope (5). The specificity of the mAb responses provides a basis for an effective diagnostic reagent. Monoclonal antibodies and binding proteins derived therefrom also have found utility as therapeutic agents.

Because of the risk that AIV infection poses to wildlife, domesticated animals and humans, there is a pressing need for a fast, specific and reliable method for detecting the virus in tissue specimens. In particular, the ability to detect the virus in preserved specimens, such as formalin fixed specimens embedded in paraffin and in frozen sections, is important to the ability to diagnose the disease and monitor its progress. To date, there have been no reports of effective methods for diagnosis of the highly pathogenic H5N1 AIV strains using H5 subtype monoclonal antibodies. Accordingly, the present invention represents a breakthrough in the diagnosis and surveillance of H5N1 and other H5 strains.

SUMMARY OF THE INVENTION

In accordance with the present invention, monoclonal antibodies and related binding proteins that are specific for linear and conformational epitopes of the H5-subtype hemagglutinin glycoprotein are provided. The mAbs to linear H5 epitopes are able to detect H5N1 virus and other H5 subtype virus strains in denatured specimens, such as formalin-fixed tissue specimens, with good specificity and sensitivity, while those that target conformational epitopes are useful for detecting the virus in frozen specimens and other biological fluids.

In particular, mAb designated 7H10 targets a linear epitope of hemagglutinin and has demonstrated high efficacy and sensitivity to viral antigen in formalin-fixed tissues, while having minimal effect on frozen tissue sections. A mAb designated 6B8 targets a conformational hemagglutinin epitope and is able to bind and recognize the viral antigen in tissues that have not been pre-treated, such as frozen tissue specimens and other biological tissues and fluid. Monoclonal antibodies designated 8F10 and 2D10 also target conformational hemagglutinin epitopes and provide similar applications as mAb 6B8.

Accordingly, the invention comprises a binding protein having substantially the immunological binding characteristics for a linear H5-subtype hemagglutinin epitope as mAb 7H10. The invention further comprises a binding protein having substantially the immunological binding characteristics for a conformational H5-subtype hemagglutinin epitope as those of mAb 6B8, 8F10 or 2D10.

In a further aspect, the invention comprises a method for detecting H5 subtype AIV in a specimen which comprises detecting the binding of AIV with a mAb or binding protein having substantially the immunological binding characteristics of mAb 7H10. In yet a further aspect, the invention comprises a method for detecting AIV in a specimen which comprises detecting the binding of AIV with a mAb or binding protein having substantially the immunological binding characteristics of mAb 6B8, 8F10 or 2D10. In particular, the invention relates to immunofluorescence assays, immunohistochemical assays and ELISA methods that utilize such binding proteins.

In another aspect, the invention relates to kits for the detection of AIV which comprise binding proteins having substantially the immunological binding characteristics of mAb 7H10 or mAb 6B8, 8F10 or 2D10.

The invention further relates to methods of treating subjects infected with an H5 AIV strain, such as an H5N1 AIV strain, which comprise administering to such subjects effective amounts of one or more monoclonal antibodies or binding proteins having substantially the immunological binding characteristics of mAb 6B8, 8F10 or 2D10.

BRIEF DESCRIPTION OF THE DRAWINGS

FIG. 1. Distribution of an mAb' titer over a period of 90 days. The data in FIG. 1 demonstrate that the mAb was able to remain stable over a substantial period of time.

FIG. 2. Cross-reactivity of H5 subtype mAbs with non-H5 subtype viruses and H5 subtype viruses measured in HI assays. The serum antibody titers against the respective viruses are indicated as follows: light shade—no HI activity, dark shade→16.

FIG. 3. Western blot analysis. Reactivities of the respective mAbs with HA1 protein of H5N1 virus expressed in *E. coli*'s total cell lysate. RPMI 1640 was used as control to the mAbs.

FIG. 7. Mapping of the epitope for 7H10. A. Schematic diagram of the hemagglutinin protein 1, showing the clone constructs for the expression of the different lengths of the HA1 fragments and their reactivities with Mab 7H10. aa, amino acid. B. Western Blot of 12 recombinant fusion proteins expressed in *E. coli* BL21. Samples were from total cell lysates. M, marker; NC, negative control; HA1, full-length HA1 protein; A-K, different fragments. C. Schematic diagram of the mutant hemagglutinin 1 fragments, showing the clone constructs for the expression of the different mutations on the HA1 fragments and their reactivities with Mab 7H10. D. Western Blot of 9 recombinant fusion proteins expressed in *E. coli* BL21. Samples were from total cell lysates. M, marker; NC, negative control; J, fragment J in B. The sequences in FIG. 7C from top to bottom are SEQ ID NO:1, SEQ ID NO:2, SEQ ID NO:3, SEQ ID NO:4, SEQ ID NO:5, SEQ ID NO:6, SEQ ID NO:7, SEQ ID NO:8 and SEQ ID NO:9.

DETAILED DESCRIPTION OF THE INVENTION

Figure 4:
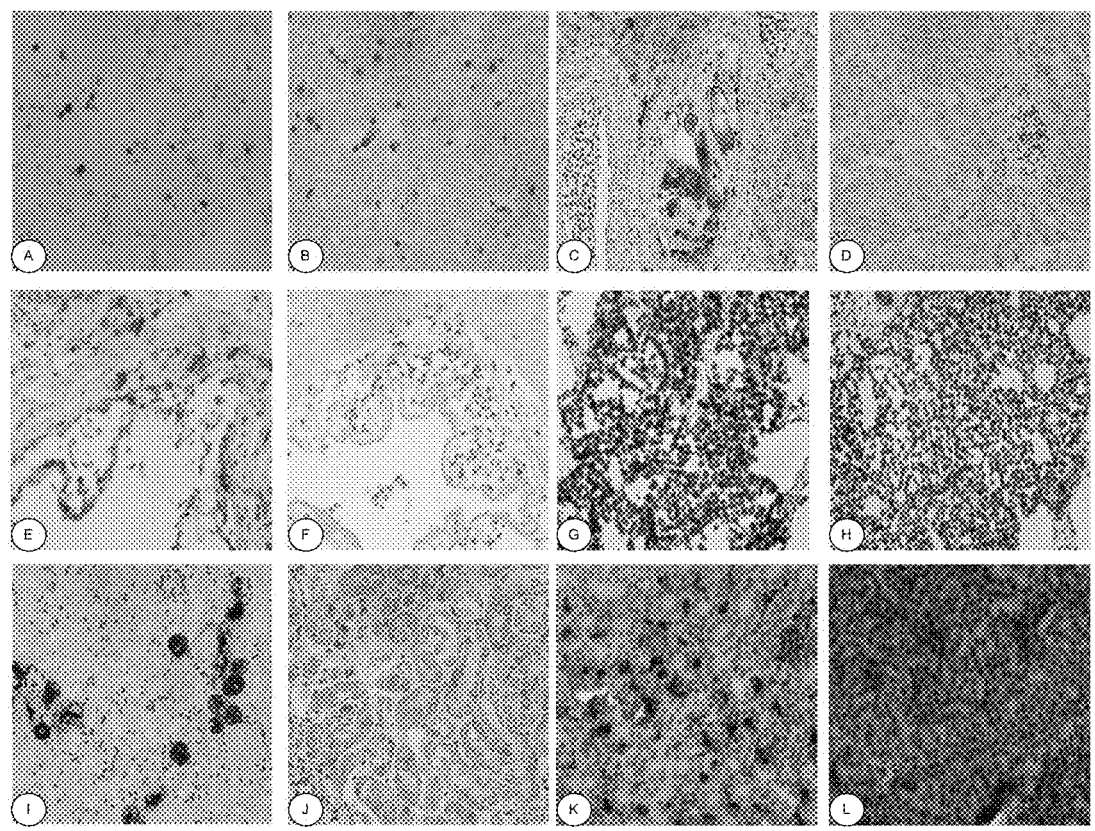
FIG. 4. Distribution of intensity of signals in different tissue specimens. Specimen was H5N1 AVI infected Magpie Robin. (Signals/lesions indicated with arrows in figure).
  a) Brain frozen section. Tissue incubated with mAb 6B8. Large intensity of positive signals was observed as multiple red spots. Lesions are seen in neurons.
  b) Brain frozen section. RPMI 1640 was applied as control to mAb 6B8. No signals were seen.
  c) Liver paraffin section. Tissue incubated with mAb 7H10. Minimal lesions were seen at the endothelium of the bile duct.
  d) Liver paraffin section. RPMI 1640 was applied as control to mAb 7H10. No signals seen.
  e) Lung paraffin section. Tissue incubated with mAb 7H10. Lesions were only seen at the lining of the epithelial tissues.
  f) Lung paraffin section. RPMI 1640 was applied as control to mAb 7H10. No signals were seen.
  g) Lung paraffin section. Tissues incubated with mAb 7H10. Lesions were seen at the alveolar tissues.
  h) Lung paraffin section. RPMI 1640 was applied as control to mAb 7H10. No signals were seen.
  i) Kidney paraffin section. Tissue incubated with mAb 7H10. Large quantity of high intensity signals were distributed throughout the kidneys cells.
  j) Kidney paraffin section. RPMI 1640 was applied as control to mAb 7H10. No signals were seen.
  k) Liver paraffin section. Tissue incubated with mAb 7H10. Lesions were seen in the hepatocytes.
  l) Liver paraffin section. RPMI 1640 was applied as control to mAb 7H10. No signals were seen.

The present invention is directed to mAbs and related antigen-binding proteins that bind specifically to the hemagglutinin envelope glycoprotein of H5 subtype of AIV. In particular, the mAb or related antigen-binding protein possesses the immunological binding characteristics of mAb 7H10 as produced by hybridoma 7H10, deposited with the American Type Culture Collection located at 10801 University Boulevard, Manassas, Va. 20110, USA, on Mar. 20, 2007, and assigned Accession Number PTA-8243, mAb 6B8, as produced by hybridoma 6B8, deposited with the American Type Culture Collection on Mar. 20, 2007, and assigned Accession Number CRL PTA-8246, mAb 8F10, as produced by hybridoma 8F10, deposited with the American Type Culture Collection on Mar. 20, 2007, and assigned Accession Number PTA-8245, or mAb 2D10, as produced by hybridoma 2D10, deposited with the American Type Culture Collection on Mar. 20, 2007, and assigned Accession Number PTA-8248. The invention further embodies those hybridomas and provides a continuous source of the mAbs and binding proteins of the invention. The invention further relates to methods for the detection and diagnosis of H5 subtype AIV infection and assay kits that comprise the mAbs or binding proteins of the invention. The invention additionally relates to methods of treating a subject infected with an H5 AIV strain through the administration of effective amounts of one or more antibodies or related binding proteins of the invention. In particular, in this embodiment the subject is infected with an H5N1 subtype of AIV. The antibodies of this invention also can be administered to subjects on the advent of a possible influenza pandemic as a precautionary measure. In this instance, effective amounts of antibodies to be administered are about half of the amounts used to treat H5 AIV infections.

Various terms are used herein, which have the following meanings:

The term "immunological binding characteristics" of a mAb or related binding protein, in all of its grammatical forms, refers to the specificity, affinity and cross-reactivity of the mAb or binding protein for its antigen.

The term "linear epitope" refers to a consecutive sequence of from about 4 to about 12 amino acids which form an antibody binding site. The linear epitopes of the mAbs of this invention preferably are in the region from about amino acid 244 to about amino acid 251 of the hemagglutinin protein encoded by the HA1 viral gene. The linear epitope, in the form that binds to the mAb or binding protein, may be in a denatured protein that is substantially devoid of tertiary structure.

The term "conformational epitope" refers to a mAb or related binding protein binding site that exists in the H5-subtype hemagglutinin glycoprotein in its native three-dimensional form.

The term "binding protein" refers to a protein, including those described below, that includes the antigen binding site of a mAb of the present invention or a mAb having the immunological binding characteristics of a mAb of the present invention.

The present invention advantageously provides methods for preparing monoclonal antibodies having the binding characteristics of mAbs 8F10 or 2D10 by immunizing an animal with AIV subtype H5N1 (PR8), preparing monoclonal antibodies having the binding characteristics of 6B8 by immunizing an animal with H5N3 protein and preparing monoclonal antibodies having the binding characteristics of 7H10 by immunizing an animal with H5 HA1 protein. Any such antigen may be used as an immunogen to generate antibodies with the desired immunological binding characteristics. Such antibodies include, but are not limited to, monoclonal antibodies, chimeric antibodies, single chain antibodies, Fab fragments, and proteins comprising the antigen binding sequence of mAb 7H10, 6B8, 8F10 or 2D10.

The mAbs of the present invention may be produced by any technique that provides for the production of antibody molecules by continuous cell lines in culture. Such methods include but are not limited to the hybridoma technique originally developed by Kohler and Milstein (1975, Nature 256: 495-497), as well as the trioma technique, the human B-cell hybridoma technique (Kozbor et al., 1983, *Immunology Today* 4:72), and the EBV-hybridoma technique to produce human monoclonal antibodies (Cole et al., 1985, in *Monoclonal Antibodies and Cancer Therapy*, Alan R. Liss, Inc., pp. 77-96). Human antibodies can be used and can be obtained by using human hybridomas (Cote et al., 1983, *Proc. Nat'l. Acad. Sci. U.S.A.*, 80:2026-2030) or by transforming human B cells with EBV virus in vitro (Cole et al., 1985, in *Monoclonal Antibodies and Cancer Therapy*, Alan R. Liss, pp. 77-96). Moreover, techniques developed for the production of "chimeric antibodies" or "humanized antibodies" (Morrison et al., 1984, *J. Bacteriol.* 159-870; Neuberger et al., 1984, *Nature* 312:604-608; Takeda et al., 1985, *Nature* 314:452-454) by introducing sequences from a murine antibody molecule of the present invention, e.g., mAb 7H10, 6B8, 8F10 or 2D10, together with genes from a human antibody molecule of appropriate biological activity can be used. Chimeric antibodies are those that contain a human Fc portion and a murine (or other non-human) Fv portion. Humanized antibodies are those in which the murine (or other non-human) complementarity determining regions (CDR) are incorporated into a human antibody. Both chimeric and humanized antibodies are monoclonal. Such human or humanized chimeric antibodies are preferred for use in in vivo diagnosis or therapy of human diseases or disorders.

According to the invention, techniques described for the production of single chain antibodies (U.S. Pat. No. 4,946, 778) can be adapted to provide single chain antibodies of the present invention. An additional embodiment of the invention utilizes the techniques described for the construction of Fab expression libraries (Huse et al., 1989, *Science* 246: 1275-1281) to allow rapid and easy identification of monoclonal Fab fragments with the desired specificity for the antibody of the present invention, or its derivatives, or analogs.

Antibody fragments that contain the idiotype of the antibody molecule can be generated by known techniques. For examples, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent. Such antibody fragments can be generated from any of the polyclonal or monoclonal antibodies of the invention.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), immunofluorescence assays and immunoelectrophoresis assays, etc. In one embodiment, antibody binding is detected by detecting a label on the primary antibody. In another embodiment, the primary antibody is detected by detecting binding of a secondary antibody or other reagent to the primary antibody. In a further embodiment, the secondary antibody is labeled. Means are known in the art for detecting binding in an immunoassay and are within the scope of the present invention.

The foregoing antibodies can be used in methods known in the art relating to the detection or localization the H5 subtype of AIV, e.g., Western blotting, ELISA, radioimmunoassay, immunofluoroescence assay, immunohistochemical assay, and the like. The techniques disclosed herein may be applied to the qualitative and quantitative determination of the H5 subtype of AIV and to the diagnosis and surveillance of animals or humans infected with the virus.

The present invention also includes assay and test kits for the qualitative and/or quantitative determination of the H5 subtype of AIV. Such assay systems and test kits may comprise a labeled component prepared, e.g., by labeling with a radioactive atom, a fluorescent group or an enzyme, coupling a label to the mAb or related binding protein of the present invention, or to a binding partner thereof. Such assay or test kits further may comprise reagents, diluents and instructions for use, as is well known to those skilled in immunoassay techniques.

In certain embodiments of the invention, such kits will contain at least the mAb or related binding protein of the invention, means for detecting immunospecific binding of said mAb or related binding protein to AIV in a biological sample, and instructions for use, depending upon the method selected, e.g., "competitive," "sandwich," "DASP" and the like. The kits may also contain positive and negative controls. They may be configured to be used with automated analyzers or automated immunohistochemical slide staining instruments.

An assay kit of the invention may further comprise a second antibody or binding protein, that may be labeled or may be provided for attachment to a solid support (or attached to a solid support). Such an antibody or binding protein may be, for example, one that binds to AIV. Such second antibodies or binding proteins may be polyclonal or monoclonal antibodies.

Monoclonal antibodies to H5-subtype hemagglutinin protein may be prepared by immunizing animals with AIV or H5 protein or fragments thereof. A preferred method involves amplification of the H5-subtype HA1 gene followed by expression of the gene, recovery and purification of H5 subtype recombinant proteins and use of the purified proteins as immunogens. For example, H5N1 AIV is propagated by inoculation of chicken embryos with available strains of the virus, followed by isolation of the viral RNA. The HA1 gene is amplified by reverse transcriptase polymerase chain reaction (RT-PCR) and then may be cloned into a baculovirus vector that is used to express H5 proteins in insect cells. The proteins so produced then can be used to immunize mice or other suitable species for production of hybridomas.

Hybridomas are screened for their ability stably to produce high affinity mAbs that are capable of specifically binding to H5 proteins and distinguish them from other AIV subtypes. In accordance with the invention, it has been found that antibodies with virus neutralization ability are able to recognize conformational epitopes in the H5-subtype hemagglutinin protein. This finding resulted from the generation of virus escape mutants in the presence of each neutralizing mAb after 1-2 rounds of selection in Madin-Darby canine kidney (MDCK) cells. The HA1 gene was cloned from these neutralization escape mutants by RT-PCR and sequenced to identify point mutations. In this panel of antibodies, 3 neutralization epitopes, namely 1, 2 and 3, were found in mAbs 6B8, 8F10 and 2D10. Neutralization-escape ability was confirmed using hemagglutination inhibition assays.

HA1 contains 338 amino acids. To study the distribution of linear epitopes on the protein, truncated and mutated fragments are advantageously tested for binding with mAbs, e.g., by Western blot or a similar technique. Linear epitopes may be identified that are binding targets for mAbs that give a good performance in detecting denatured H5 subtype protein, such as that occurring in formalin-fixed tissue, using immunohistochemical staining methods. Mapping of the H5 subtype mAbs in this manner provides a platform for further study and a more effective clinical diagnosis of the infectious H5N1 AIV.

The present invention also has provided a better understanding of the antigenic structure of the hemagglutinin molecule of H5-subtypes of AIV. The mAbs and related binding proteins of the invention provide a means for detecting this highly pathogenic virus in denatured tissues fixed in paraffin as well as in frozen sections and biological specimens.

The ability to detect the virus in paraffin sections is of great importance. Under most circumstances, H5N1 antigens in infected tissue sections are destroyed by the fixation process. Formalin and ethanol have the potential to remove the lipid envelope and envelope glycoproteins, including hemagglutinin, hence increasing the difficulties in viral antigen detection. Therefore, this form of diagnosis has the potential to provide a safer and more precise diagnosis on H5 infected animal and human tissues.

As illustrated by the examples presented below, mAb 7H10 is highly efficacious and sensitive to viral antigen in formalin-fixed tissues while having a minimal effect on frozen tissue sections. This antibody allows infected regions to be easily visualized under the light microscope. Antibody 7H10 does not have hemagglutination inhibition or viral neutralization activities; however, it exhibits positive results in immunofluorescence assay and in Western blot analysis, strong bands that correspond to the recombinant H5NI-HA protein (MW 36 kDa) are observed.

In contrast, mAbs 6B8, 8F10 and 2D10 are highly efficacious on frozen tissue sections, but do not detect antigen in formalin-fixed tissues. These results imply that the two groups of mAbs react with different viral epitopes. Through epitope mapping, mAb 7H10 was determined to target linear epitopes. It could only detect the viral antigens when the tissues were subjected to intensive heat treatment. Under such harsh antigen retrieval methods, surface proteins of the virus were destroyed and left nucleoprotein of the H5N1 virus exposed. Therefore, mAbs that target linear epitopes did not work as well on frozen tissue sections.

Monoclonal antibodies 6B8, 8F10 and 2D10 were determined by epitope mapping to target conformational epitopes of the H5N1 virus. These antibodies were able to bind and to recognize these viral antigens without prior treatments to the tissue sections.

The differences in staining intensity on different tissue specimens observed in immunohistochemical analysis reflect that the level of viral infiltration differs from tissue to tissue. For instance, in brain and kidney tissue, individual cells were deeply stained and there was also a large distribution of stained cells in brain and kidney tissues. These findings indicate that lungs might not be the most severely infected organs at the later stage of viremia. Previously, intensive lesions in lungs of H5N1 infected animals have been reported (2, 13, 14). However, the present findings indicate that lungs have fewer lesions than kidneys. Because tissue specimens utilized in the experiments leading to this invention were obtained from birds at a late stage of infection, these results may suggest that lungs normally have a high level of viremia at early stages of infection and that during later stages virus will be spread and concentrated at the kidneys. These results therefore indicate that diagnostic specimens from animals suspected of infection with H5N1 AIV should include brain and kidney tissues as well as lung tissue.

This invention provides convenient, highly specific and sensitive means for detecting H5 subtype AIV. One such means is the ELISA format. In a preferred embodiment mAb 7H10 and 6B8 are used as capture antibodies. It has been found that this combination provides high optical density readings in detection of H5-subtype AIVs in comparison to either antibody alone or in other combinations. While not bound by any particular theory, a possible explanation of these results is that the two antibodies react with different epitopes on the HA1 protein and are of different antibody subclasses, therefore providing multiple binding sites.

Monoclonal antibodies against conformational epitopes maintain important biological functions, such as hemagglutination inhibition and neutralization activity, while mAbs against linear epitopes are also advantageous for diagnostic uses. Therefore, the application of mAbs 7H10 and 6B8, which were against linear and conformational epitopes, respectively, and combine the immunological properties of IgG and IgM in antigen-antibody interaction, might contribute greatly to the high sensitivity of ELISA procedures. The approach of using two mAbs also may be used to develop other immunological methods to detect H5 viruses, such as, for example, by dot-blot and in situ hybridization formats.

The preferred ELISA test of this invention is able to detect HA antigen from H5N1 avian influenza virus infecting poultry in China and humans in Vietnam, indicating the utility of the invention for detecting both avian and human H5N1 infections.

The H5-subtype mAbs of this invention have at least three advantages over other current methodologies as diagnostic tools. First, the mAbs are highly specific for the highly infectious H5-subtype AIV. This specificity has been verified in an assortment of H5N1-infected tissue specimens from years 2002 to 2006 obtained from various sources. Such highly specific monoclonal antibodies represent a breakthrough in the field of avian influenza diagnosis. Second, the ability of these mAbs to detect and accurately localize H5 viral antigen in infected formalin-fixed tissue as well as in serological tests such as HI and IFA represent a distinct advantage. Third, these mAbs provide a safe and convenient diagnostic approach for the detection of H5 AIV. Their ability to detect viral antigens in paraffin sections facilitates transport and diagnosis of infected specimens that will not infect humans or have the potential to release infectious virus particles into the environment. Moreover, frozen section slides can be cryogenically stored for long periods of time and facilitate further diagnosis and surveillance of infections.

Another embodiment of the invention relates to neutralization escape mutants of H5 avian influenza. The term "neutralization escape mutant" refers to a mutant virus raised by point mutations in the genes encoding hemagglutinin which caused antigenic drift in the H5 virus and affect neutralization epitopes. A neutralization escape mutant can evade neutralization by certain monoclonal antibodies that are effective in neutralizing its parent virus. In manual screening for escape mutants, a parental virus is incubated with a certain neutralization antibody and inoculated into a host, such as MDCK cells or chicken embryos. After 2-3 rounds of screening, the escape mutant for the neutralization mAb is cloned and subjected to HA1 gene sequencing. The mutated amino acid is determined by alignment with the parental virus sequence, and the mutated site indicates exactly one of the amino acids comprising the neutralization epitope recognized by the neutralization mAb.

In the present invention, 6B8 escape mutants arise from H5N3 AIV by the 6B8 neutralization monoclonal antibody. 8F10 escape mutants arise from H5N1 (PR8) AIV by the 8F10 neutralization antibody and 2D10 escape mutants arise from H5N1 (PR8) AIV by the 2D10 neutralization monoclonal antibody. Mutation sites are listed in Example 3, Table 3, below.

Neutralization escape mutants are different from their parental virus in that they no longer can be recognized by certain neutralization antibodies which specifically bind to the parent virus. In view of this, these mutants can be used to immunize mice for new monoclonal antibody production in accordance with the teachings above. Among the new mAbs, a monoclonal antibody which exactly recognizes the mutated epitope can be screened out which then can be used to provide complementary surveillance to avian influenza viruses other than the parental virus. By repeating this process through several generations, further escape mutants can be found and further neutralizing antibodies obtained. These antibodies can be used in the methods of the present invention.

In a further embodiment of the invention, the antibodies and related binding proteins of the invention can be administered to treat subjects suffering from an H5 AIV infection, particularly an infection from an H5N1 subtype of AIV. The antibodies and related binding proteins of the invention also can be administered to subjects as a preventive measure in the event of an influenza pandemic or threatened pandemic. The antibodies and related binding proteins can be administered in a single dose or in repeated administrations, optionally in a slow release form. Administration can be made by any means that enables the antibody to reach its site of action in the body of the subject being treated, e.g., intravenously, intramuscularly, intradermally, orally or nasally. Typically, the antibody is administered in a pharmaceutically acceptable diluent or carrier, such as a sterile aqueous solution, and the composition can further comprise one or more stabilizers, adjuvants, solubilizers, buffers, etc. The exact method of administration, composition and particular dosage will be determined and adjusted at the time to therapy, depending upon the individual needs of the subject, taking into account such factors as the subject's age, weight, general health, and the nature and extent of his or her symptoms, as well as the frequency of treatment to be given. Generally, the dosage of antibody administered is within the range of about 0.1 mg/kg to about 1 mg/kg body weight when the antibody is administered to treat patients suffering from an H5 AIV infection. Typically, the dosage is reduced by about half, i.e. to within the range of about 0.05 mg/kg to about 0.5 mg/kg body weight, when administered as a preventive measure.

A single antibody or binding protein of the invention can be administered for therapeutic purposes or a combination of two or more can be administered. If antibodies to one or more generations of neutralization escape mutants have been produced, such antibodies and the 6B8, 8F10 and/or 2D10 antibodies described above can be administered as therapeutic antibody "cocktails."

The following examples are provided to illustrate a preferred mode of practicing the invention. The invention is not limited to the details of the examples, but is commensurate with the full scope of the appended claims.

EXAMPLE 1

Production of Hybridomas

Virus designated H5N1/PR8 was obtained from the Center for Disease Control (USA). It is a non-pathogenic recombinant H5N1 influenza virus that contains the HA and NA genes of an AIV H5N1 virus that infected a human in Vietnam (A/Vietnam/1203/2004). Another AIV subtype, H5N3 (A/chicken/Singapore/97) was obtained from AgriFood & Veterinary Authority (AVA) of Singapore. These two virus stocks were used to infect 9 to 11-day-old embryonated chicken eggs (Chew's Poultry Farm, Singapore) and allowed to replicate for two generations. Allantoic fluid from the embryonated chicken eggs was then drawn, and viral titer was determined using hemagglutination assay (HA). Purification of these H5N1 and H5N3 viruses was performed by centrifugation of virus-containing allantoic fluids at 10,000 rpm for 30 minutes to remove debris, followed by ultracentrifugation of the supernatant at 40,000 rpm for 3 hours. The virus pellet was resuspended in PBS.

Monoclonal antibodies (IgG and IgM) were purified from clarified fluids using protein A affinity column (Sigma Aldrich; St. Louis, Mo., USA) ImmunoPure® IgM purification kit (Pierce Biotechnology; Rockford, Ill., USA) in accordance with manufacturer's instructions. The concentrations of IgG and IgM were measured by using an ND-1000 spectrophotometer (Nanoprop Technologies; Wilmington, Del., USA).

Inactivated H5N1 AVI (A/goose/Guangdong/97) was used as a source of RNA to amplify HA1 gene by RT PCR for epitope mapping. Viral RNA was isolated from virus-infected cells using TRIzol® LS reagent (Invitrogen) as specified by the manufacturer. Reverse transcription and PCR were performed with specific primers for the HA1 gene of H5 subtypes. The PCR product then was sequenced by standard procedures. Amplified DNA was cloned into pQE-30 vector, which in turn was used for transformation of *E. coli* BL-21 competent cells. For baculovirus-mediated protein expression, the genes then were cloned into pFASTBAC Ta vector to construct a recombinant baculovirus containing H5N1 HA1 gene. The baculovirus was subsequently used to infect SF9 insect cell line for the amplification of the recombinant virus. For selection of escape mutants, H5N1 AIV (A/Vietnam/1203/2004/H5N1) was used as the source of RNA.

These purified H5-subtype viruses or purified H5 HA1 protein from baculovirus then were used to immunize 6 to 8 week old female BALB/c mice intramuscularly twice at intervals of two weeks. Each animal was inoculated with 20-60 μg of purified H5-subtype AIV emulsified with an equal volume of adjuvant (SEPPIC, France). Three days before cell fusion the mice were then given an intraperitoneal booster of the same dosages of viruses. Blood sera from the mice were then screened by Western blot and mice having the highest antibody titer were selected for cell fusion. Splenocytes obtained from the selected mice were combined with SP2/0 myeloma cells in a 1:10 ratio in 50% polyethylene glycol (Sigma, mol. wt. 3350) to fuse the cells and produce hybridomas (21).

All experiments with live virus were conducted in a biosafety level 3 containment laboratory (20) that has met the CDC/NIH biosafety requirements, as specified in Biosafety in Microbiological and Biomedical Laboratories (BMBL) 4th Edition. The experiments also complied with applicable WHO requirements as well as those approved by the AVA and Ministry of Health (MOH) of Singapore.

EXAMPLE 2

Screening of Hybridomas

Hybridoma culture supernatants were screened by hemagglutination inhibition (HI) test and immunofluroescence assay (IFA) as described below.

Hemagglutination Inhibition Test.

H5N1/PR8 virus obtained from CDC was used to infect 9 to 11-day old embryonated chicken eggs (Chew's Poultry Farm, Singapore) and incubated at 35° C. for 72-96 hours. After propagation of the virus, allantoic fluid from the chicken embryos was extracted and used as H5N1 viral antigen. The respective hybridoma culture supernatants were subjected to HI test as described previously (15) using chicken erythrocytes for agglutination and 4 hemagglutination units of H5N1/PR8 virus strain. Serial dilutions of hybridoma supernatants were initially diluted 1:50 and were then incubated with 4 HA units of the H5N1/PR8 virus propagated in chicken embryos (inactivated with 0.1% beta-propiolactone) and a 0.5% (vol/vol) suspension of chicken erythrocytes per well. Antibody titers corresponding to the reciprocal of the highest dilution that inhibited hemagglutination were expressed as geometric mean titers (GMTs).

Immunofluroescence Assay:

Madin Darby Canine Kidney cells (MDCK) cells that were grown in a 96-well plate for 24 hours were infected with H5N1/PR8, H5N2 and H5N3 viruses from the respective allantoic fluid. The wells at alternate rows were used for negative controls (uninfected MDCK cells). The 96-well plate was placed in a humidified 35° C., 5% $CO_2$ incubator for 18-22 hours. When the infected cells reached a cytopathic effect (CPE) of 75%, they were fixed with 100 μl of absolute ethanol for 10 minutes at room temperature. Cells in 96-well plates were then washed 3 times with PBS, pH 7.4. Subsequently, the fixed cells were incubated with 50 μl of the respective hybridoma supernatants for 1 hour at 37° C. After 3 washings, the antigens were reacted and incubated with fluorescein isothiocyanate (FITC)-conjugated anti-mouse Ig (1:100 DAKO, Denmark) for 1 hour at 37° C. For a more discriminating way of screening the mAbs by IFA, additional controls were employed. As mentioned earlier, uninfected MDCK cells were used as negative controls. As an additional negative control, cells were incubated with RPMI 1640. For positive control, serum from immunized mouse at a 100-fold dilution was used. By comparing MDCK cells incubated with the respective hybridoma supernatants with the different controls, the hybridoma supernatants which gave positive staining were selected for cloning by limiting dilution. A stable mAb producing hybridoma was obtained by this procedure.

EXAMPLE 3

Characterization of H5-Subtype Monoclonal Antibodies

Stability of mAbs.

The hemagglutination inhibition test was performed on the respective hybridoma supernatants obtained at different periods of time (7th, 30th, 45th, 60th, 70th, and 90th days) to gauge the stability of the cell lines. Dilution was performed to calculate the end point. Hybridoma supernatant of mAb 6B8 had an HI titer of 29. The titer remained stable even on the $90^{th}$ day (see FIG. 1). Thus, the hybridoma clone secreting mAb to H5 antigens was able to maintain a high titer value for a long period of time.

Isotyping of mAb.

Isotyping was performed using a mouse mAb isotyping kit (Amersham Bioscience, England). (Data not shown.) The isotypes of 6B8, 8F10 and 2D10 were determined as IgM and 7H10 was determined as IgG1.

MAbs Specificity Analysis.

The H5-subtype mAbs were cross-reacted with related H5 subtypes, AIV H5N2 and H5N3 and also with non-H5 subtype influenza viruses, H3N2, H4N1, H7N1, H9N2 and H10N5. The HI test was used to test the cross-reactivities. The results, illustrated in FIG. 2, showed that there were no cross-reactions when H5-subtype mAbs were exposed to non-H5 subtype viruses H3N2, H4N1, H7N1, H9N2 and H10N5. MAbs 6B8, 2D10 and 8F10 had cross-reactivity with H5N2 and H5N3. Table 1 shows the efficacy of the respective H5 subtype mAbs on frozen and formalin-fixed tissues. In Table 1, a semi-quantitative score was assigned to the intensities of the observed signals in infected tissues as follows: absent (−), mild (+), moderate (++), strong (+++) and very strong (++++). RPMI 1640 was used as the control for H5-subtype mAbs, and chicken tissue infected with Newcastle disease was used as the control for H5N1 infected tissue. AI and H5 mAbs from other sources were used for comparison to the H5-subtype mAbs of the invention.

TABLE 1

| mAbs | Derivation of mAbs | Frozen Sectioned Tissues | Paraffin Sectioned Tissues |
| --- | --- | --- | --- |
| 6B8 | F59/04/98 | ++++ | − |
| 7H10 | A/goose/Guandong/97 | − | ++++ |
| AI | Other Sources | ++ | − |
| H5 | Other Sources | ++ | − |

Immunohistochemical staining, discussed below, further confirmed the specificity of these H5 subtypes mAbs to H5N AIV.

Virus Neutralization of mAbs.

MDCK cells and 10-day-old embryos were used for determination of 50% tissue culture infections dosage ($TCID_{50}$) and 50% embryo infectious dosage ($EID_{50}$), respectively. MDCK cells ($2 \times 10^4$/ml) were allowed to grow to 70%-90% of confluence. Allantoic fluids infected with the respective viruses, using a series of dilutions factors from $10^{-1}$ to $10^{-8}$, were tested for $TCID_{50}$ and $EID_{50}$ by infecting both MDCK cells at their exponential phase (highest sensitivity to virus infection) and 10-day old chicken embryos. Uninfected MDCK cells and allantoic fluid were used as negative controls. The cells were incubated at 35° C. and CPE was observed. Using Reed and Muench mathematical technique (9), the infectivity titer was expressed as $TCID_{50}/100$ μl and $1000\ EID_{50}/200$ μl, and the respective viruses were each diluted to having $100\ TCID_{50}$ and $500\ EID_{50}$ in 50 μl and 100 μl, respectively. Serially diluted mAb 6B8 was able to neutralize the final concentration of $100\ TCID_{50}$ and $500\ EID_{50}$ of viruses in infected MDCK cell and embryos. See Table 2. The data presented in Table 2 also shows that mAb 6B8 was capable of producing neutralizing activity with H5N1 viruses. The numbers in Table 2 reflect the highest dilution ratio of H5N1 viruses at which the mAbs were still able to detect and neutralize the virus at a final concentration of 100 TCID50 and 500 EID50 of viruses in infected MDCK cell and embryos.

TABLE 2

| Infected Cells | mAbs | | | |
|---|---|---|---|---|
| | 6B8 | 7H10 | 8F10 | 2D10 |
| MDKC Cells | 130 | 0 | 200 | 200 |
| Embryo | 40 | 0 | 160 | 40 |

Selection of Escape Mutants.

Serial 10-fold dilutions of the parental virus were mixed with equal volumes of mAb. After incubation for 1 hour at room temperature, the mixture was inoculated onto a monolayer of MDCK cells in DMEM medium containing 200 μg/ml TPCK-treated trypsin (Sigma) and 0.001% DEAE-dextran (Sigma). After 7 days at 35° C., the virus supernatant was collected and subjected to further selection. For selection of escape mutants, H5N1 AIV (A/Vietnam/1203/2004/H5N1) was used as the source of RNA. The escape mutants were clones to be compared with parental sequence. An escape mutant was selected using neutralizing mAb 6B8. The point mutation responsible for the resistance to mAb 6B8 neutralization was determined to occur at nucleotide 614 on HA1 sequence. The mutation involves the change of nucleotide 614 from "A" to "C", which results in mutation at amino acid 205 from lysine into threonine. The ability of this mutation to allow the mutant virus to escape mAb 6B8 neutralization was verified by neutralization assay and hemagglutinin inhibition assay. This result indicated the mAb 6B8 targets an epitope containing amino acid 205 on hemagglutinin. Two other neutralization epitopes were identified for mAbs 8F10 and 2D10 respectively by the same methods. The results are set forth in Table 3, which shows the location of mAb neutralization epitopes on the hemagglutinin molecule of AIV (A/Vietnam/1203/2004 H5N1).

TABLE 3

| Escape Mutant | Epitope | Nucleotide | Nucleotide Change | Amino Acid | Amino Acid Change |
|---|---|---|---|---|---|
| 6B8a | 1 | 614 | A→C | 205 | Lys→Thr |
| 6B8b | 1 | 615 | G→T | 205 | Lys→Asn |
| 8F10a | 2 | 629 | C→T | 210 | Pro→Leu |
| 8F10b | 2 | 628 | C→T | 210 | Pro→Ser |
| 2D10a | 3 | 524 | C→T | 175 | Thr→Ser |
| 2D10b | 3 | 523 | A→G | 175 | Thr→Ala |

Western Blot.

The recombinant H5N1-HA1 protein was subjected to 10% SDS-PAGE. The separated proteins were immobilized to nitrocellulose paper. The membrane was blocked with 5% non-fat milk in PBS containing Tween® 20 nonionic surfactant for 1 hour. After washing with PBS Tween® 20 nonionic surfactant, three times at 5 min each, the membrane was incubated with the respective mAbs followed by HRP-conjugated rabbit anti-mouse Ig (1:2000). The membrane was then developed with 3,3'-diaminobenzidine (DAB) for 5 min. The reaction was stopped by rinsing with PBS Tween® 20 nonionic surfactant. After each incubation, reagents were washed by PBS Tween® 20 nonionic surfactant, three times at 5 min each. MAb 7H10 was used as positive control because the latter was derived from purified recombinant HA1, while RPMI 1640 was used as negative control. As illustrated in FIG. 3, H5-subtype MAb 7H10 is able to react with the recombinant H5N1-HA1 protein. Bands formed on the nitrocellulose membrane were 36 kDa. This is equivalent to the molecular weight of the recombinant protein. On the other hand, mAbs 6B8, 8F10, 2D10 and RPMI 1640 gave negative results. Since 6B8 and the other mAbs target the viral protein in its native form, this group of mAbs will not be able to detect the viral protein by Western blot. SDS-PAGE used in Western blot will unfold the native proteins and linearize them, hence making detection impossible.

EXAMPLE 4

Mapping the Linear Epitope of mAb 7H10

The HA1 gene of H5-subtype AIV was dissected into 3 overlapping fragments by PCR and expressed as a histidine fusion protein. Analysis by Western blot with mAb 7H10 revealed that the epitope is primarily found in the overlapping region of fragments B and C (amino acids 201-266). To locate the C terminus of this epitope, 8 truncated fragments were designed and screened with mAb 7H10 (FIGS. 7a and b) by Western blot. Amino acid 251 on HA1 was found to be the C-terminal amino acid of the epitope for 7H10. To locate the N terminus of this epitope, 8 mutated fragments was designed and screened with mAb 7H10. Among the 8 mutants, amino acid 240-247 on HA1 was changed into alanine individually by certain primers. According to the result of Western blot, the N-terminal amino acid in the epitope is amino acid 244 on HA1 (FIGS. 7c and d). These results indicated that the linear epitope targeted by Mab 7H10 is located at amino acids 244 to 251 inclusive on hemagglutinin of H5-subtype AIV.

EXAMPLE 5

Immunohistochemistry

Thirty H5N1-infected tissue specimens from year 2002-2006 were tested. They included different types of tissue organs such as brain, kidney, liver, lung and pancreas. They were in the form of either paraffin-sectioned specimens or frozen sections. A commercially available immunoperoxidase staining system (Dako Cytomation EnVision+System-HRP (AEC)) was used for these specimens. The staining technique involves two steps (16) to recognize bound antibodies (20) based on a horseradish peroxidase labeled polymer which is conjugated with secondary antibodies. Because this kit does not contain avidin or biotin, non-specific endogenous avidin-biotin activity is reduced substantially.

Paraffin-Sectioned.

The results of the staining of paraffin-sectioned specimens are shown in FIG. 4. Very strong positive signals were observed in infected kidney tissues. There was a wide distribution of signals seen throughout the kidney tissues, and each signal had a very high intensity. On the contrary, the lungs did not reflect such strong signals in terms of distribution and intensity. Only the epithelium lining of lung tissues were lightly stained. As for liver tissue, signals were sparsely distributed. However, each signal that was detected was intense. It was also noted that for infected liver tissues, signals were usually detected along the epithelium of bile ducts. On closer examination, the bile ducts were observed to be infected by flukes. These results show that mAb 7H10 is an H5-subtype AIV monoclonal antibody that is able to retrieve H5 antigens from H5N1 infected formalin-fixed tissues.

Frozen-Sectioned.

Figure 5:
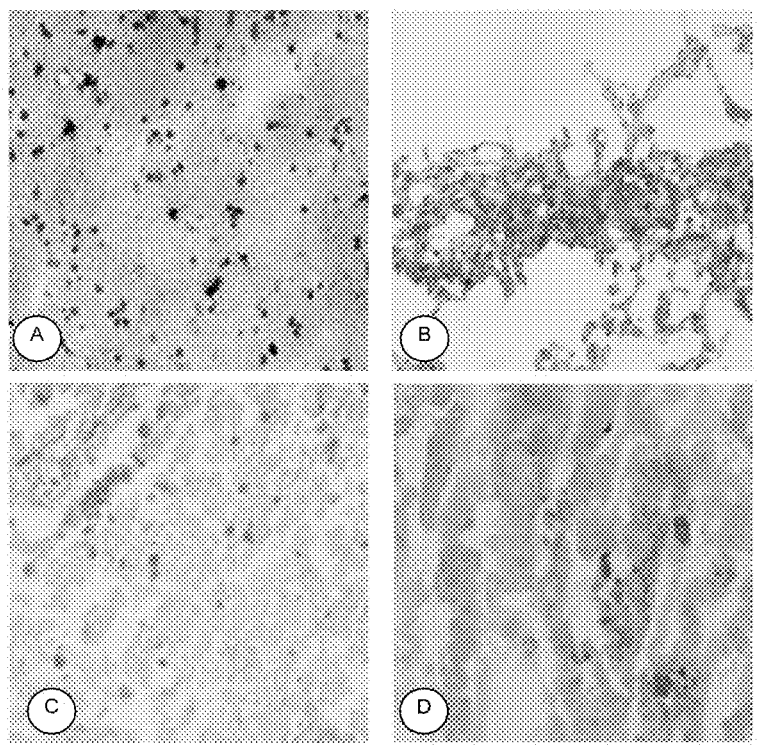
FIG. 5. H5 subtype mAbs were able to detect signals from H5N1 infected tissues dated back to year 2002.
  a) House Crow's brain tissue.
  b) Pond Heron's lung tissue.
  c) Grey Heron's brain tissue.
  d) Chicken's brain tissue.

The results of staining frozen-sectioned specimens are shown in FIG. 5. Antibody 6B8 could detect strongly positive signals on all specimens from different years. The photomicrographs of these stained tissues clearly show that it was the neurons of these infected brain tissues that were stained. For both frozen and paraffin sections, it was clearly seen that only nucleus in the tissues were stained regardless of the type of tissues. The principal lesions (20) of birds infected with H5N1 virus were kidney and brain tissues. The data in Table 1 supra demonstrates the ability of the mAbs of the invention to distinguish H5-subtype AIV from avian influenza from other sources.

EXAMPLE 6

Development of AC-ELISA

Monoclonal antibodies 7H10 and 6B8 were evaluated in an ELISA procedure as follows: 6B8 (IgM) was serially diluted in half-log increments and used to coat 96-well flat-bottomed microtiter plates (Nunc, Demark). Capture antibodies were suspended in 50 µl of carbonate buffer (73 mM sodium bicarbonate and 30 mM sodium carbonate). The microtiter plates were then incubated at 37° C. for 1 hour or at 4° C. overnight. The plates were washed three times with phosphate-buffered saline (PBS) containing 0.05% Tween® 20 nonionic surfactant (PBS-T) between all subsequent incubation steps, and all dilutions were made in PBST containing 1% nonfat milk. The plates were blocked by incubation with 50 µl of blocking solution (5% nonfat milk in PBS-T) at 37° C. for 1 hour, rinsed and incubated with 50 µl of purified recombinant H5N1 recombinant HA1 (100 ng) or H5 AIV at 37° C. for 1 hour. After rinsing, 50 µl of guinea pig monospecific antibody IgG (diluted 1:480) was added, incubated for 1 hour at 37° C., washed and incubated with 50 µl of HRP-conjugated rabbit anti-guinea pig immunoglobulin diluted 1:1000. Color was developed by the addition of 50 µl of freshly prepared substrate solution (o-phenylenediamine (OPD)), and absorbance at 490 nm was read with an ELISA reader (Tecan, Switzerland). Optimal working dilutions of mAbs and monospecific antibodies were determined by checkerboard titration. Optimization conditions were determined by comparing H5 AIV (H5N1, H5N2, H5N3) and non-H5 AIV (H7N1 and H9N2) reactions to achieve the highest signal-to-noise ratio for this assay. The signal-to-noise ratio was calculated by dividing the absorbance of homologous antigen by that of heterologous antigen.

Figure 6:
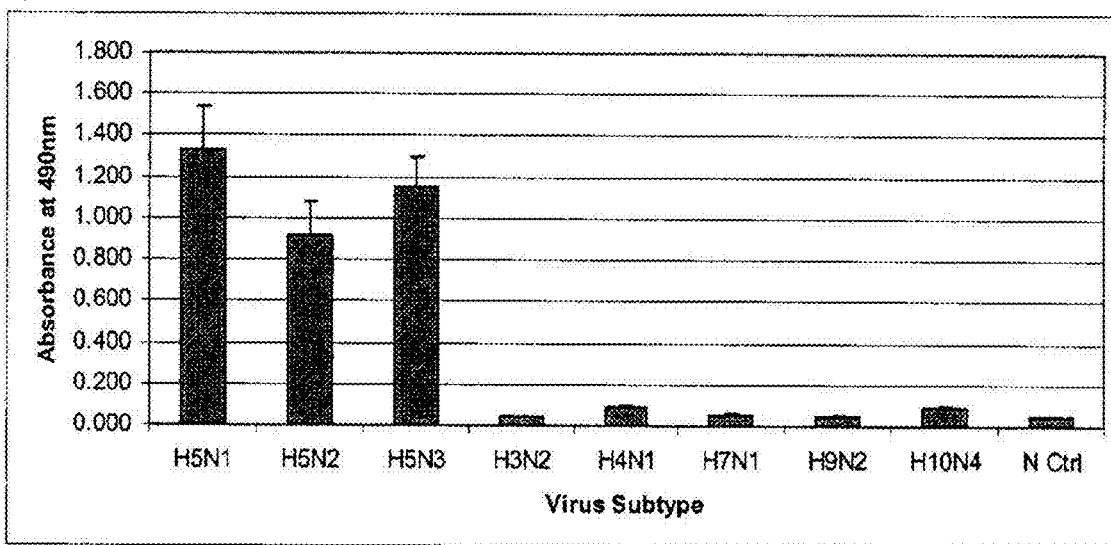
FIG. 6. Reactivity of capture and detector antibody in AC-ELISA format. (a) Different AIV subtypes were tested using an AC ELISA test. The specificity of this test is shown when only H5 AIV produces positive results. "N Ctrl" is the negative control where no virus was added to the well. (b) Different H5 AIV were serially diluted with PBS and tested in the AC ELISA. Using 0.100 as the cut-off value between positive and negative results, the minimum amount of H5 AIV that can be detected with the AC ELISA test was averaged out to be approximately 0.5 HA Unit, 7H10 and 6B8.
Figure 6:
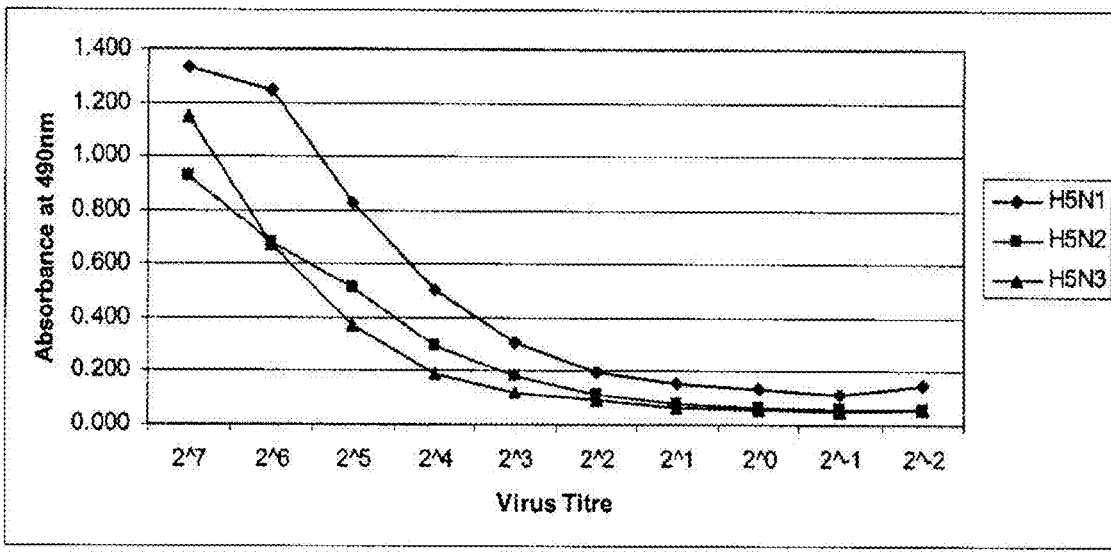

Monoclonal antibody 6B8 was used as a capture antibody and also as a detection antibody in AC-ELISA. Monoclonal antibody 6B8 showed stronger reactivity than other monoclonal antibodies in the ELISA. Such AC-ELISA by 6B8 is specifically applicable to H5 subtype AIV detection and does not react with any other AIV subtypes (FIG. 6a). The detection limit of the AC-ELISA is less than 0.5 HA Units (FIG. 6b). After checkerboard titration, the optimal antibody concentration for the capture ELISA were determined to be 600 ng per well for each mAb as capture antibody and 800 ng per well of detector polyclonal antibody.

REFERENCES

1. A. N Hamir, G. M., D. T. Galligan, S. W. Davis. D. E Granstrom, J. P. Dubey. 1993. Immunohistochemical study to demonstrate Sarcocystis neurona in equine protozoal myeloencephalitis. *Journal of Veterinary Diagnostic Investigation,* 5:418-422.
2. Cauthen, A. N., D. E. Swayne, S. Schultz-Cherry, M. L. Perdue, and D. L. Suarez 2000. Continued circulation in China of highly pathogenic avian influenza viruses encoding the hemagglutinin gene associated with the 1997 H5N1 outbreak in poultry and humans. *J. Virol.,* 74:6592-9.
3. Crawford, J., B. Wilkinson, A. Vosnesensky, G. Smith, M. Garcia, H. Stone, and M. L. Perdue. 1999. Baculovirus-derived hemagglutinin vaccines protect against lethal influenza infections by avian H5 and H7 subtypes. *Vaccine,* 17:2265-74.
4. Dilbeck, P. M., and T. F. McElwain. 1994 Immunohistochemical detection of *Coxiella bumetti* in formalin-fixed placenta. *J. Vet. Diagn. Invest.,* 6:125-7.
5. Eli Benjamin, R. C., Geoffrey Sunshine. 2000. *Immunology: A short course,* 4th ed. A John Wiley & Sons, Inc.
6. Evensen, O., O. B. Dale, and A. Nilsen. 1994 Immunohistochemical identification of *Renibacterium salmoninarum* by monoclonal antibodies in paraffin-embedded tissues of Atlantic salmon (*Salmo salar* L), using paired immunoenzyme and paired immunofluorescence techniques. *J. Vet. Diagn. Invest.,* 6:48-55.
7. Fitzgerald, S. D., W. M. Reed, and R. M. Fulton. 1995. Development and application of an immunohistochemical staining technique to detect avian polyomaviral antigen in tissue sections. *J. Vet. Diagn. Invest.,* 7:444-50.
8. Fouchier, R. A., T. M. Bestebroer, S. Herfst, L. Van Der Kemp, G. F. Rimmelzwaan, and A. D. Osterhaus. 2000. Detection of influenza A viruses from different species by PCR amplification of conserved sequences in the matrix gene. *J. Clin. Microbiol.,* 38:4096-5101.
9. Grimes, S. E. 2002. A basic laboratory manual for the small-scale production and testing of I-2 Newcastle disease vaccine RAP Publication 2002/22 136 pg.
10. Horimoto, T., N. Fukuda, K. Iwatsuki-Horimoto, Y. Guan, W. Lim, M. Peiris, S. Sugii, T. Odagiri, M. Tashiro, and Y. Kawaoka. 2004. Antigenic differences between H5N1 human influenza viruses isolated in 1997 and 2003. *J. Vet. Med. Sci.,* 66:303-5.
11. http colon slash slash www dot who dot int slash csr slash disease slash avian influenza slash country slash cases table 2006 04 27 slash en slash index dot html.
12. Iwasaki, T., S. Itamura, H. Nishimura, Y. Sato, M. Tashiro, T. Hashikawa, and T. Kurata. 2004. Productive infection in the murine central nervous system with avian influenza virus A (H5N1) after intranasal inoculation. *Acta Neuropathol. (Berl),* 108:485-92.
13. Lu, X., T. M. Tumpey, T. Morken, S. R. Zaki, N. J. Cox, and J. M. Katz. 1999. A mouse model for the evaluation of pathogenesis and immunity to influenza A (H5N1) viruses isolated from humans. *J. Virol.,* 73:5903-11.
14. Mase, M., K. Tsukamoto, T. Imada, K. Imai, N. Tanimura, K. Nakamura, Y. Yamamoto, T. Hitomi, T. Kira, T. Nakai, M. Kiso, T. Horimoto, Y. Kawaoka, and S. Yamaguchi. 2005. Characterization of H5N1 influenza A viruses isolated during the 2003-2004 influenza outbreaks in Japan. *Virology,* 332:167-76.

15. Dose-response relationship after immunization of volunteers with a new, surface-antigen-adsorbed influenza virus vaccine. *J. Infect. Dis.*, 135:423-31.
16. Renee Larochelle, R. M. 1995. Comparison of immunogold silver staining (IGSS) with two immunoperoxidase staining systems for the detection of porcine reproductive and respiratory syndrome virus (PRRSV) antigens in formalin-fixed tissues. *Journal of Veterinary Diagnostic Investigation*, 7:540-543.
17. Robert G. Webster, A. G. 1994. *Encyclopedia of Virology*, 2:709-724.
18. Ross, T. M., Y. Xu, R. A. Bright, and H. L. Robinson. 2000. C3d enhancement of antibodies to hemagglutinin accelerates protection against influenza virus challenge. Nat. Immunol., 1:127-31.
19. Stevens, J., O. Blixt, T. M. Tumpey, J. K. Taubenberger, J. C. Paulson, and I. A. Wilson. 2006. Structure and receptor specificity of the hemagglutinin from an H5N1 influenza virus. *Science*, 312:404-10.
20. Tanaka, H., C. H. Park, A. Ninomiya, H. Ozaki, A. Takada, T. Umemura, and H. Kida. 2003. Neurotropism of the 1997 Hong Kong H5N1 influenza virus in mice. *Vet. Microbiol.*, 95:1-13.
21. Yokoyama W. M, C. J. E., A. M Kruisbeek, D. H Margulies, E. M. Shevach, W. Strober (eds). 2001. Production of monoclonal antibodies. *Currents protocols in immunology:* 2.5.1-2.6.9.
22. Zhou, N. N., D. A. Senne, J. S. Landgraf, S. L. Swenson, G. Erickson, K. Rossow, L. Liu, K. Yoon, S. Krauss, and R. G. Webster. 1999. Genetic reassortment of avian, swine, and human influenza A viruses in American pig: *Virol.*, 73:8851-6.

What is claimed is:

1. A monoclonal antibody 2D10 as produced by hybridoma 2D10 which is deposited with the American Type Culture Collection with Accession Number PTA-8248.

2. A method for detecting H5 subtype avian influenza virus in a biological specimen which comprises contacting the specimen with monoclonal antibody 2D10 as produced by hybridoma 2D10 which is deposited with the American Type Culture Collection with Accession Number PTA-8248.

3. The method of claim 2, which further comprises contacting the biological specimen with a detector binding protein that specifically binds to the envelope glycoprotein of an H5 subtype of avian influenza virus, wherein the monoclonal antibody 2D10 is a capture binding protein and the detector binding protein contains or is conjugated to a detectable element.

4. The method of claim 3, wherein the detector binding protein is a monoclonal antibody.

5. The method of claim 3, wherein the 2D10 monoclonal antibody is immobilized onto a solid surface.

6. The method of claim 3, wherein the detector binding protein contains a radioactive atom, is conjugated to a fluorescent molecule, or is conjugated to an enzyme.

7. A kit for detecting H5 subtype avian influenza virus in a biological specimen, wherein the kit comprises the monoclonal antibody 2D10 as produced by hybridoma 2D10 which is deposited with the American Type Culture Collection with Accession Number PTA-8248, together with reagents for the detection of binding of said monoclonal antibody 2D10 to hemagglutinin glycoprotein of an H5 subtype of avian influenza virus.

8. The kit of claim 7, which further comprises a detector binding protein that specifically binds to the envelope glycoprotein of an H5 subtype of avian influenza virus, wherein the monoclonal antibody 2D10 is a capture binding protein and the detector binding protein contains or is conjugated to a detectable element.

9. The kit of claim 8, wherein the detector binding protein is a monoclonal antibody.

10. The kit of claim 8, wherein the 2D10 antibody is immobilized onto a solid surface.

11. The kit of claim 8, wherein the detector binding protein contains a radioactive atom, is conjugated to a fluorescent molecule, or is conjugated to an enzyme.

* * * * *